(12) United States Patent
Godara et al.

(10) Patent No.: US 9,554,765 B2
(45) Date of Patent: Jan. 31, 2017

(54) POSITIONING TOOL

(75) Inventors: Neil Godara, Milton (CA); Robert Harrison, Milton (CA)

(73) Assignee: Avent, Inc., Alpharetta, GA (US)

( * ) Notice: Subject to any disclaimer, the term of this patent is extended or adjusted under 35 U.S.C. 154(b) by 1026 days.

(21) Appl. No.: 12/524,074

(22) PCT Filed: Jan. 22, 2008

(86) PCT No.: PCT/CA2008/000087
§ 371 (c)(1),
(2), (4) Date: Jul. 22, 2009

(87) PCT Pub. No.: WO2008/089537
PCT Pub. Date: Jul. 31, 2008

(65) Prior Publication Data
US 2010/0099980 A1 Apr. 22, 2010

Related U.S. Application Data

(60) Provisional application No. 60/886,096, filed on Jan. 22, 2007.

(51) Int. Cl.
*A61B 5/05* (2006.01)
*A61B 6/00* (2006.01)
(Continued)

(52) U.S. Cl.
CPC .............. *A61B 6/506* (2013.01); *A61B 6/12* (2013.01); *A61B 17/3403* (2013.01); *A61B 90/39* (2016.02); *A61B 90/92* (2016.02); *A61B 90/96* (2016.02); *A61B 90/11* (2016.02); *A61B 2017/00261* (2013.01); *A61B 2090/061* (2016.02); *A61B 2090/3916* (2016.02); *A61B 2090/3937* (2016.02); *A61B 2090/3966* (2016.02)

(58) Field of Classification Search
CPC ....... A61B 6/12; A61B 6/506; A61B 17/3403; A61B 19/54; A61B 19/201
USPC ... 600/407, 424; 604/48, 180, 264, 268, 513
See application file for complete search history.

(56) References Cited

U.S. PATENT DOCUMENTS 3,836,776 A 9/1974 Gullekson
4,583,538 A 4/1986 Onik et al.
(Continued)

FOREIGN PATENT DOCUMENTS

EP 0979637 2/2000
WO WO 2006/062806 6/2006

OTHER PUBLICATIONS

International Search Report (PCT/CA2008/000087)—3 pages.
Extended European Search Report for PCT/CA2008/000087, Sep. 21, 2012.

*Primary Examiner* — Joseph M Santos Rodriguez
(74) *Attorney, Agent, or Firm* — Dority & Manning, P.A.

(57) ABSTRACT

A positioning tool aids in the positioning of at least one instrument at a subcutaneous treatment site visible via a medical imaging device. The positioning tool includes a penannular member, at least one spacing member having a proximal end attached to the penannular member and a distal end spaced from the proximal end, and at least one aligning portion attached to the at least one spacing member. The aligning portion is configured for aligning the tool with a target visible via the medical imaging device. A kit includes a plurality of the tools. A method includes use of the tool.

23 Claims, 15 Drawing Sheets

(51) Int. Cl.
    *A61B 6/12*         (2006.01)
    *A61B 17/34*      (2006.01)
    *A61B 17/00*      (2006.01)

(56) References Cited

U.S. PATENT DOCUMENTS

| | | |
|---|---|---|
| 4,803,974 A | 2/1989 | Powell et al. |
| 4,860,331 A | 8/1989 | Williams et al. |
| 5,285,785 A | 2/1994 | Meyer et al. |
| 5,755,746 A | 5/1998 | Lifshey et al. |
| 6,036,696 A | 3/2000 | Lambrecht et al. |
| 6,269,148 B1 | 7/2001 | Jessop et al. |
| 6,293,966 B1 * | 9/2001 | Frantzen ................. 623/1.15 |
| 6,471,721 B1 * | 10/2002 | Dang ..................... 623/1.34 |
| 6,926,733 B2 * | 8/2005 | Stinson .................. 623/1.15 |
| 2003/0187431 A1 | 10/2003 | Simonson et al. |
| 2004/0068315 A1 * | 4/2004 | Chandrasekaran et al. . 623/1.15 |
| 2004/0082913 A1 * | 4/2004 | Spohn et al. ............. 604/160 |
| 2004/0116802 A1 | 6/2004 | Jessop et al. |
| 2004/0171986 A1 * | 9/2004 | Tremaglio et al. ........ 604/116 |
| 2006/0145871 A1 * | 7/2006 | Donati et al. ............ 340/572.8 |
| 2008/0039866 A1 * | 2/2008 | Stetz et al. .............. 606/129 |

* cited by examiner

POSITIONING TOOL

CROSS-REFERENCES TO RELATED APPLICATIONS

The present application is a 35 U.S.C. §371 application of PCT Application No. PCT/CA08/00087, filed on Jan. 22, 2008, which claims priority to U.S. Provisional Application Ser. No. 60/886,096 filed on Jan. 22, 2007.

TECHNICAL FIELD

This invention relates to tools for aiding in the positioning of medical instruments. More specifically the invention relates to tools that indicate a position on the surface of the body relative to an internal body structure.

SUMMARY OF THE INVENTION

In one broad aspect, embodiments of the present invention comprise a positioning tool for aiding in the positioning of at least one instrument at a subcutaneous treatment site visible via a medical imaging device, the positioning tool comprising: at least one aligning portion for aligning the tool with a target visible via the medical imaging device, at least one spacing member and at least one instrument positioning portion; the of least one aligning portion being visible via the medical imaging device and spaced from the at least one instrument positioning portion by the at least one spacing member; the at least one instrument positioning portion being visible via the medical imaging device for providing an indicator for positioning the at least medical one instrument at the treatment site.

As an additional broad aspect, embodiments of the present invention provide a method of positioning at least one medical instrument at a subcutaneous treatment site visible using a medical imaging device, the method using a positioning tool located on a surface of a patient's body, the positioning tool comprising at least one aligning portion and at least one instrument positioning portion, the method comprising: substantially aligning the positioning tool with the target by visualizing the aligning portion and the target using the medical imaging device; inserting the at least one medical instrument into the patient's body; and positioning the at least one medical instrument such that a treatment portion of the at least one medical instrument is substantially aligned with the instrument positioning portion, by visualizing the treatment portion and the instrument positioning portion using the medical imaging device.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
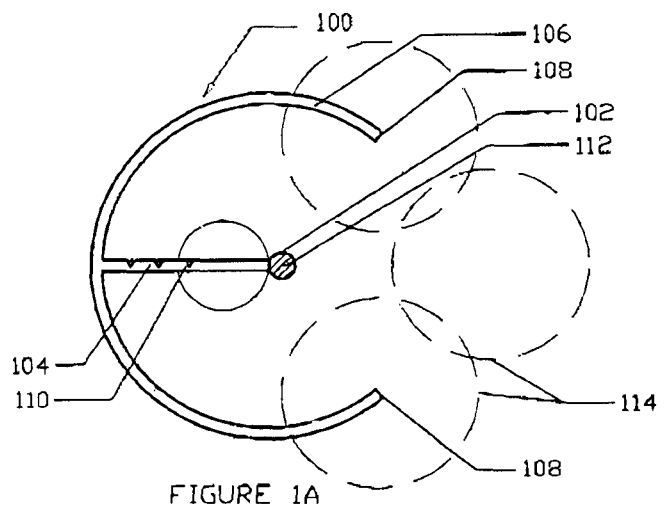
FIGS. 1A-1B, 1D are top views of an penannular shaped positioning tool, in accordance with one embodiment of the present invention.

With specific reference now to the drawings in detail, it is stressed that the particulars shown are by way of example and for purposes of illustrative discussion of certain embodiments of the present invention only. In this regard, no attempt is made to show structural details of the invention in more detail than is necessary for a fundamental understanding of the invention, the description taken with the drawings making apparent to those skilled in the art how the several forms of the invention may be embodied in practice.

In one embodiment of the present invention a positioning tool is disclosed for placement on a patient's skin for aligning with a target location on an internal target for placement of a treatment device at the treatment site. An example of the embodiment of the present invention comprises a positioning tool for use in treatment of pain in the Sacroiliac region of a patient's body. The sacrum is a large, triangular bone at the base of the spine and at the upper and back part of the pelvic cavity, where it is inserted like a wedge between the two hip bones. Its upper part connects with the last lumbar vertebra and with ilia of the hip bone on each side. The vertebral (sacral) canal runs throughout the greater part of the bone. It lodges the sacral nerves, and its walls are perforated by the anterior and posterior sacral foramina through which these nerves pass. In order to treat pain, the lateral branch nerves arising from the posterior rami of the sacral spinal nerves are targeted from S1 to S3. The positioning tool 100 shown in FIG. 1 is essentially shaped in the form of an Epsilon. The positioning tool comprises on alignment portion 102 containing a radiopaque indicator. a member 104 that extends from the edge to indicate a radial distance and a member along the circumference 106 to the indicate the circumference along the radius. The member 106 defines edges 108, referred to as instrument positioning portions. Members 104 and 106 are collectively referred to as spacing members, in the various embodiments described herein, any reference to members connecting alignment portions and instrument positioning portions should be understood to be spacing members. In addition, in the embodiments described herein, the alignment portions and the instrument positioning portions are radiopaque so as to be visible under fluoroscopic imaging. In some embodiments, at least a portion of the spacing members may also be radiopaque.

Figure 10A:
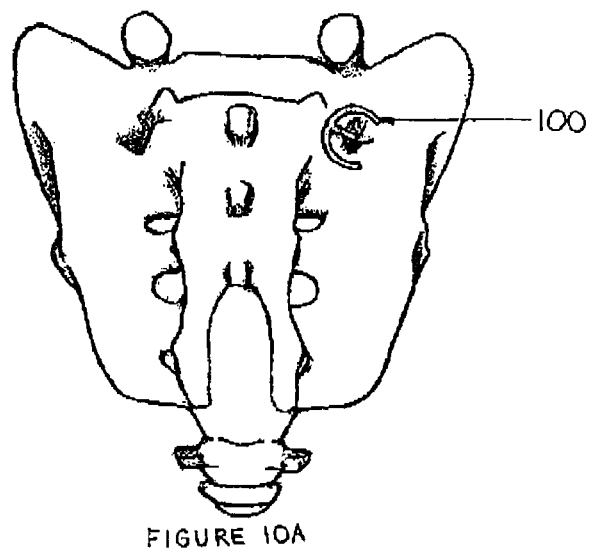
FIG. 10A is a top view of an Epsilon shaped positioning tool in accordance with an embodiment of the present invention, depicting the position of the positioning tool with respect to the sacrum.

In the embodiment of the present invention a method is described for positioning a treatment device in the vicinity of the sacral foramen for lesioning a target nerve. The positioning tool is placed on the patient's body under fluoroscopy. The alignment portion 102 of the of the positioning tool 100 is placed against the lateral edge of the foramen. Unlike other bone structures in the body that can be easily viewed under fluoroscopy, however, the sacrum lies such that the lower intestines are right under it. This causes varying radiopacities along the intestines as the image is constantly changing. It can be hard for the physician to guess where to place the positioning tool and only an extremely trained eye can estimate the location without an aid. Thus, to visualize the foramen under fluoroscopy a finder needle 112 is used. The use of the needle can prevent mistakes caused by misplacement of the positioning tool and consequently, the treatment device. A fine gauge needle similar to an injection needle is dropped into the hole of the foramen. The positioning tool 100 is then aligned such that the aligning member 102 of the middle spacing member 104 is aligned with the needle. FIG. 10A is on illustration of the method of the present invention depicting the position of the partially penannular positioning tool 100 with respect to the sacrum. It indicates the positioning of the device at the sacral foramen. It should be noted however, that the device is positioned on the patient's skin (not shown).

Three lesion locations are defined by the positioning tool, when it is positioned correctly. One function of the positioning tool is that it acts as a ruler and defines the distance along the member 104, from the edge of the member 104 to the circumferential member. In one example of the present embodiment this distance is defined as 10 mm. This radial distance defines the distance away from the foramen where the nerve is most likely to be found and hence the distance at which the lesion will be most effective. Secondly, the positioning tool defines and helps to visualize the effective treatment locations. In order for the positioning tool to achieve this function, the positioning tool is rotated into the desired position. The spinal needle 112 is treated like the centre of a clock, with members positioned at the 2:30, 4:00 and the 5:30 positions. The tip of the middle member 104 or the alignment portion 102 of the spacing member is positioned at the 4:00 O Clock mark. Whereas, the instrument positioning portions 108 of the circumferential member are positioned at the 2:30 and 5:30 mark. These portions 108 define the locations where the lesions need to be formed and indicate the position to which the treatment devices should be inserted. The angle between spokes on the positioning tool is about 100 degrees, ensuring that the lesion spots are spaced about 50 degrees apart. Additional features of the embodiment of the present invention include evenly spaced notches 110 on the spacing member 104 of the positioning tool which provide feedback. As an example, the spacing member contains about three notches. The notches provide incremental measurements and provide a better resolution. Usually, only the 1 cm mark is used on the positioning tool. However, the notches help to increase utility. In some individuals there is very little space between where the ileum of the hipbone is overhanging the sacrum. The lesion formed in this case will be closer to the foramen. The notches provide a more accurate measurement of where the lesion is formed, for example ¾ cm away from the sacral foramen. The positioning tool can be used on the opposite side of the sacrum by rotating it to align with the sacral foramen on the opposite side of the patient's body. The lesion locations in this instance are defined at the 6:30, 8:00 and 9:30 positions of the clock.

Figure 1B:
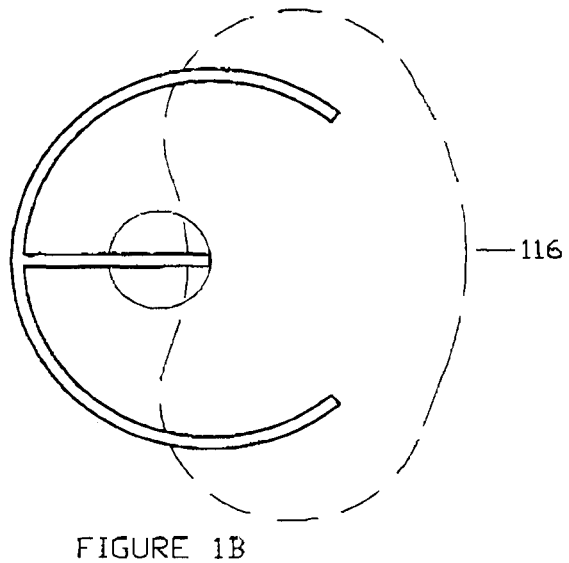

In the embodiment of the present invention as illustrated in FIG. 1A, individual lesions 114 are created at the treatment locations defined by the portions 108. The combined resultant lesion 116 is illustrated in FIG. 1B.

FIG. 2 illustrates one embodiment of the present invention showing an image of the positioning tool 200 of the present invention as may be obtained using a medical imaging device such as X-ray fluoroscopy. The positioning tool comprises a reniform shape comprising a hollow interior with an outer framework defined by a circumferential member 202, which may be referred to, in this embodiment, as an alignment portion. In general, the alignment portion is the portion of the tool used to align with a subcutaneous target within the patient's body, while the instrument positioning portion is the portion used to indicate the final position of the treatment devices.

The positioning tool further comprises one or more spacing members 204, defined as projections that extend from the circumferential member towards the hollow interior at least partially therethrough. Each spacing member is defined by a lateral edge 206, which is an instrument positioning portion. In some embodiments the spacing member may span across the entire width of the hollow interior. In some embodiments the spacing members do not extend integrally from the device and may be otherwise attached.

Figure 2A:
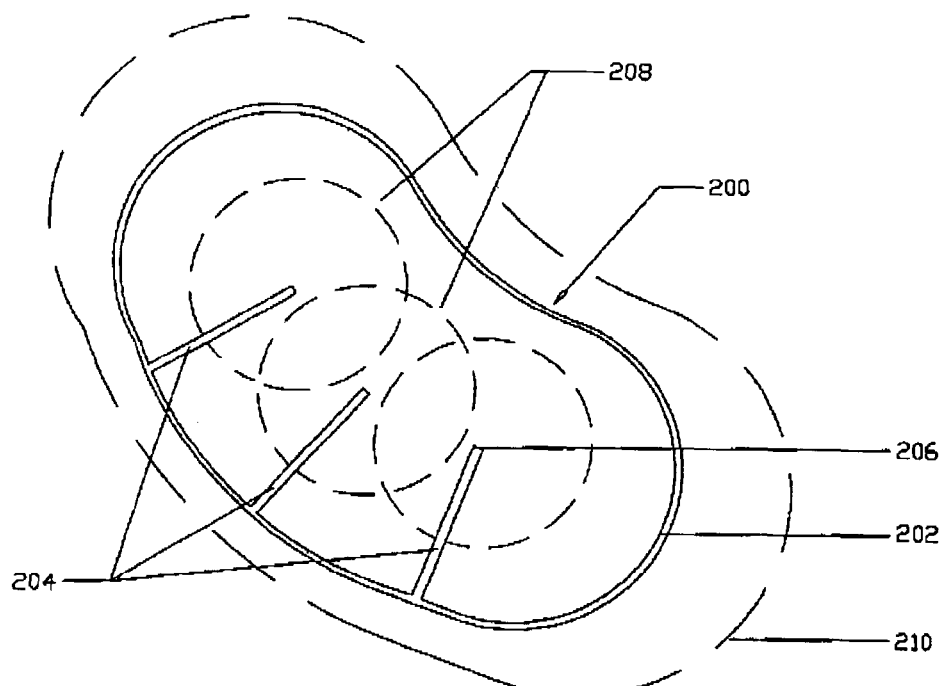
FIGS. 2A-2B are top views of a reniform positioning tool, in accordance with one embodiment of the present invention.
Figure 2B:
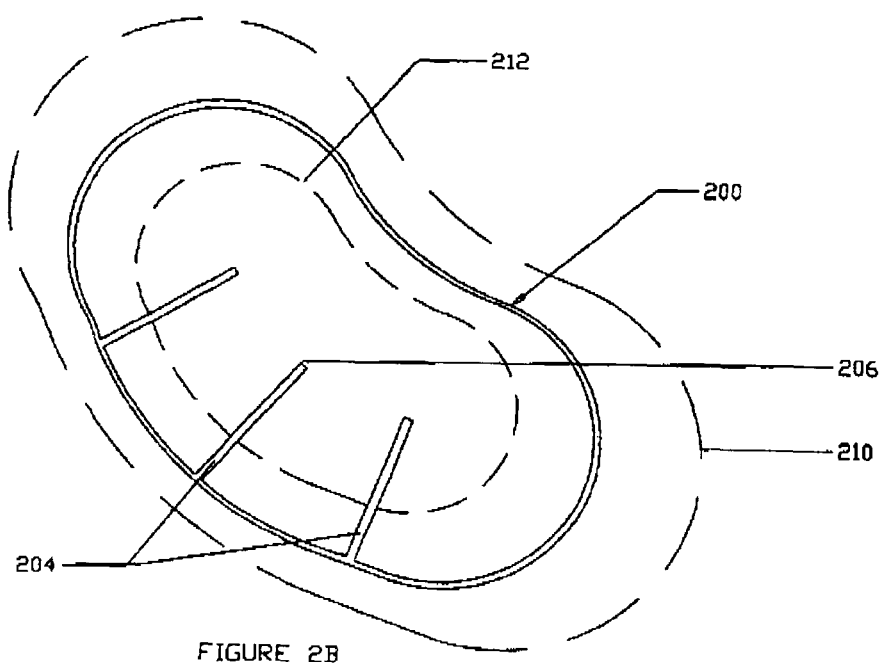

In an example of an embodiment of the present invention a marking device is disclosed for placing in the lumbar region of a person's spine. An L-shaped region on the fluoroscope indicates the region that needs to be lesioned. The lesion needs to be created in the region where the transverse process meets the superior articulate process. This forms a gulley where the nerve is located. In order to target the nerve, the entire area is lesioned. The reniform positioning tool 200 is placed on a vertebra of the lumbar region, where the transeverse articular process meets the superior articulate process, when the structures are viewed at an angle of about 15 degrees to 45 degrees with respect to the saggital plane. This region is defined as the "neck" of the superior articular process and marks the area where the nerve is most likely to be situated. The objective is to place one or more lesion across the neck of the superior articular process in order to encompass the target nerve. This area 210 defines the desired lesion size. The probes need to be positioned such that a volume of tissue following the curvature of the bone is lesioned. This area extends about 5 mm from the surface of bone. When measured from the neck, the desired lesion area extends about 30 percent along the SAP surface and about 20 percent along the TP surface. The preferred lesion sites are defined by the lateral edges 206 of the spacing members 204. The individual lesions 208 are formed of these sites and the resulting lesion 212 is indicated in FIG. 2B.

Figure 3:
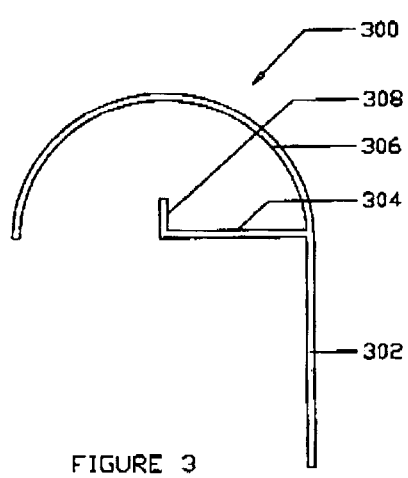
FIG. 3 is a top view of a J-shaped positioning tool, in accordance with an embodiment of the present invention.
Figure 4:
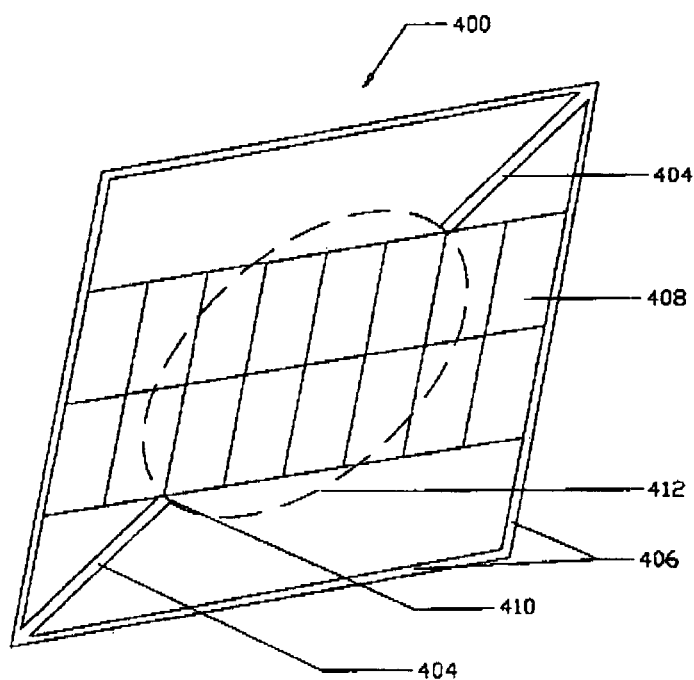
FIG. 4 is a top view of a rhomboid shaped positioning tool, in accordance with one embodiment of the present invention.

In another embodiment of the present invention a marking device is disclosed for placing in the thoracic region of a person's spine as illustrated in FIG. 3. The device comprises an aligning member 302 for aligning with the subcutaneous target; a member 304, and a circumferential member 306, collectively referred to as a spacing member. Tool 300 further comprises on instrument positioning portion 308 for providing an indicator for positioning a treatment device at the target site.

Figure 10B:
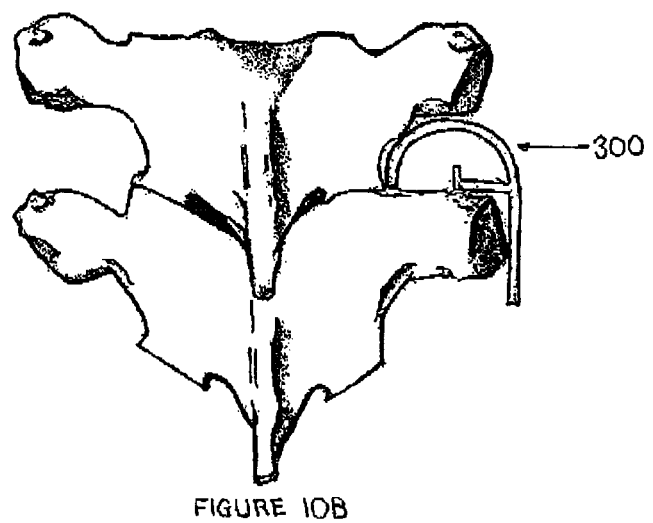
FIG. 10B is a top view of a positioning tool, in accordance with one embodiment of the present invention, for use in positioning a treatment device in the thoracic region of a patient's spine.

In a further embodiment of the present invention, a method is disclosed for using the positioning tool in the thoracic region of a patient's body. The positioning tool 300 is oriented on a vertebra of the thoracic region, more specifically, on the superolateral corner of the transverse process. The physician ensures that the aligning member 302 is substantially parallel to the lateral aspect of the transverse process. The device is then positioned by sliding it along the top edge of the transverse process such that the spacing member 304 is adjacent to the corner aspect of the transverse process. The desired lesion size is defined by the region encapsulated by the circumferential member 306, which outlines the zone where the nerve is likely to be found. The nerve path is defined by the area bounded by the curve of the circumferential member 306 and the transverse process. In one example of the embodiment of the present invention, the circumferential member is defined as having a radius of about 5 mm. The desired target lesion size is about a 9 mm sphere. In one example, the spacing member has a minimum length of about 3 mm and allows for easy maneuvering of the device and does not obscure the view of any anatomical features. The length of the spacing member and the dimensions of the tool are limited such that they do not cloud the physician's view of the anatomy or hinder in the placement of the treatment device. FIG. 10B is on illustration of the method of the present invention depicting the position of the J-shaped positioning tool 300 with respect to the thoracic vertebrae. It indicates the positioning of the treatment device with respect to the corner aspect of the transverse process. It should be not however, that the device is positioned on the patient's skin (not shown).

In another embodiment of the present invention a marking device is disclosed for placing in the cervical region of a person's spine. The positioning tool 400, is of a substantially rhomboid shape. The outer perimeter of the positioning tool is defined by members 406, referred to as aligning portions. The space between edges 410 of the spacing members 404 defines the region to be lesioned. Edges 410 are referred to as instrument positioning portions.

In a still further embodiment of the present invention a method is disclosed for using the positioning tool in the cervical region of a patient's spine. The positioning tool 400 is oriented on a vertebra of the cervical region, more specifically, on the waist of the articular pillar. If the articular pillar is sectioned into four quadrants, the target lesion size is defined as the middle two quadrants 408 or 50 percent of the area enclosed by the rhomboid positioning tool 400. The area 408 can be visualized as the area between the spacing members 404. The physician then creates lesions at areas aligned with instrument positioning portions 410 in order to fill the area 408. The resulting lesion 412 that is formed will follow the contour of the bone.

A general problem encountered is the projection of a distorted image of the positioning tool on the sacrum. This occurs when the positioning tool is not aligned with the sacrum under fluoroscopy. When the positioning tool is tilted with respect to the sacrum a shortened projection is formed on the sacrum and correct lesion locations cannot not be marked. The tilt can occur due to skin contours on the back of a patient. In order to get an image projection with the same dimension as the positioning tool, the tool needs to be parallel to the sacrum and needs to lie in the same plane as the sacrum. This can be achieved by adjusting the angle of the positioning tool with respect to the skin such that it compensates for the tilt.

An embodiment of the present invention comprises a positioning tool that can be used to judge the degree of misalignment of the tool with respect to the internal body structure. The thickness of the positioning tool (vertical height) can be increased such that when the positioning tool is viewed from the top, it con be observed as a thin outline on the fluoroscopic screen. However, when the positioning tool is viewed from the side it appears as a black circle on the fluoroscope. This information can be used to adjust the plane of the epsilon. The amount of thickness of shadow indicates the degree of misalignment of the tool. The fluoroscope is fixed such that it is level with the plane of the sacrum and once the positioning tool is adjusted to match this plane.

Figure 5A:
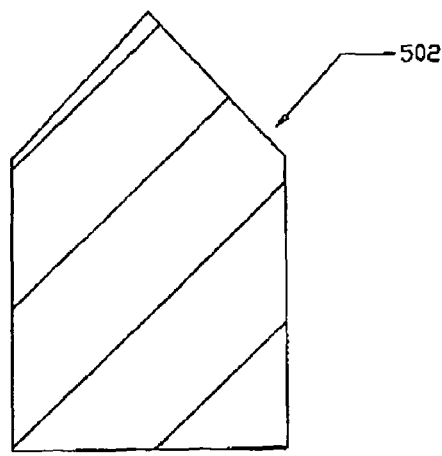
FIGS. 5A-C are side views of a member of a positioning tool, in accordance with the embodiment of the present invention, depicting the cross-sectional area.
Figure 5B:
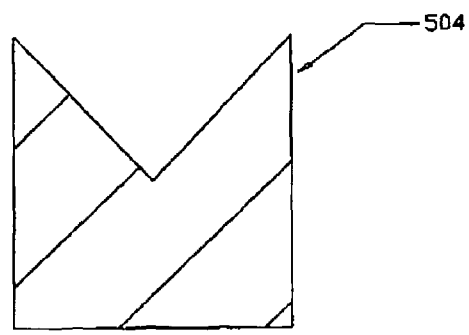
Figure 5C:
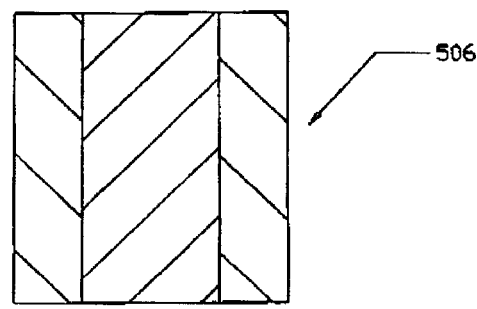

Another example of the feature of the present invention comprises a positioning tool with varying radiopacities in the cross-section as shown in FIGS. 5A-5C. As an example of this embodiment of the present invention, the positioning tool is composed of steel and the cross-section 502 comprises a triangular portion over top a rectangular portion as shown in FIG. 5A. This allows the central segment of the positioning tool to appear darker as it comprises the most steel. If the marking device is tilted, then it becomes maximally thick at the edge. This enables the user to ascertain if the positioning tool is optimally positioned. As an alternate embodiment the cross section 504 comprises less material in the centre and greater at the edges as illustrated in FIG. 5B. As an alternate embodiment of the present invention, the varying radiopacity in the cross-section is created through the use different metals that are more or less radiopaque as illustrated in the cross-section 506 in FIG. 5C. In conclusion, the varying radipacity in the cross-section can be observed by taking material away, or alternatively, having a constant thickness of material but of different compositions. These embodiments enable the user to ensure that the positioning tool is aligned with the sacrum in the radiographic image. Cross-sections 502, 504 and 506 may, in some embodiments, be taken through a portion of the spacing member(s). In other embodiments, for example as in FIG. 2, the cross-sections may be taken through the aligning portion(s).

Figure 6A:
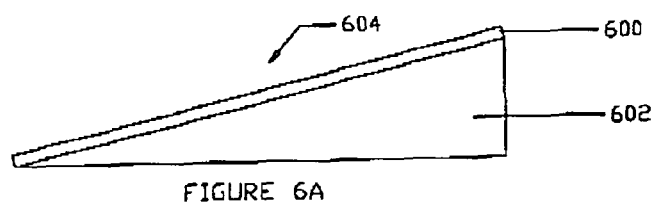
FIGS. 6A-6B are side views of alternate embodiments of a shim for adjusting the tilt of the positioning tool, in accordance with one embodiment of the present invention.
Figure 6B:
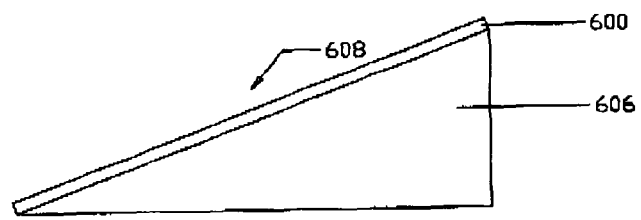
Figure 6C:
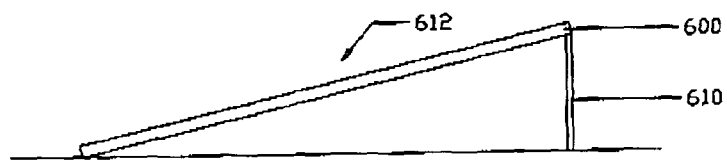
FIG. 6C is a side view of a positioning tool with a single projection, in accordance with an embodiment of the present invention.
Figure 6D:
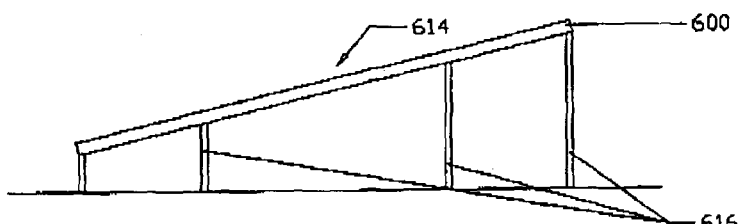
FIG. 6D is a side view of a positioning tool with a plurality of projections, in accordance with one embodiment of the present invention.

An embodiment of the present invention comprises a positioning tool with an adjustable means to alter the tilt. As an example of this feature of the present invention, a triangular boot, shoe or shim 602 can be used to align the positioning tool 600 as shown in the combined assembly 604 of FIG. 6A. In one embodiment of the present invention the boot has an angle of about 30 degrees. In various embodiments of the present invention, the boot 602 can have varying sizes with an angle that varies from about 5 degrees to about 50 degrees. In another example of the present embodiment the boot 606 has an angle of about 60 degrees, as shown in the device assembly 608, illustrated in FIG. 6B. The shoe can be used to increase the tilt of the positioning tool about 5 to 10 degrees at a time until the desired image is obtained on the fluoroscope. In one example of the present embodiment the boot comprises a plastic material to prevent interference with the fluoroscope image. The boot may be removable from the spacing member or aligning portion. In one embodiment of the present invention, the positioning tool comprises an inherent angle. The height of the positioning tool increases gradually along the transverse cross-section of the device. In a further embodiment of the present invention the positioning tool 600 comprises a vertical cleat 610 that aids in tilting the positioning tool as shown in the device assembly 612 shown in FIG. 6C. In a still further embodiment of the present invention the positioning tool assembly 614 comprises cleats 616 integral to the device 600 affixed to the lower surface of the device as shown in FIG. 6D. In one example of the present embodiment the cleats are about 5 mm long. A minimum amount of force can be applied to the cleats on one side of the positioning tool, effectively tilting the device. In one example the cleats may be otherwise attached to the positioning tool for example by using an adhesive or by welding or other affixing means.

Figure 7:
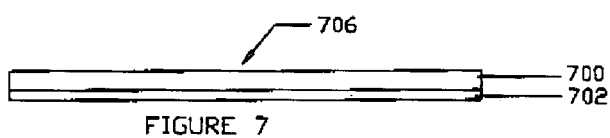
FIG. 7 is a side view of a positioning tool, in accordance with the present invention, comprising a coating on the external surface.

In one embodiment of the present invention the positioning tool comprises an attachment means to affix the device to the patient's skin. The cleats 616 also function to secure the positioning tool to the skin. In an alternate embodiment of the present invention a positioning tool with adhesive means is provided 706. As illustrated in FIG. 7, the positioning tool 700 comprises an adhesive 702 applied to the lower surface, to aid in attaching the device to the patient's skin. In one example, the adhesive comprises a double sided tape. In another example, an adhesive for coating metal is applied to the lower surface of the device. In some embodiments the device may be spray coated with adhesive.

In one embodiment of the present invention the surface of the positioning tool can be treated to increase the traction between the device and the skin. Silicone can be applied to the positioning tool. In some embodiments a liquid dispersion of silicone in a solvent is applied to the surface of the device. The entire surface of the positioning tool is dip coated and the positioning tool is then left to dry. This process creates a non-slip surface.

In a still further embodiment of the present invention a method is disclosed for using a positioning tool to aid in the treatment of a tumor. The tumor is imaged using a medical imaging technique such as an MRI or a CT scan. After the tumor has been located, different sized positioning tools can be placed on the patient's skin to fit the tumor size. After a positioning tool has been found that has dimensions matching the tumor, it can be placed such that it overlays the fluoroscopic image. The positioning tool, when positioned properly, will help to determine the extent of the lesion that will be formed. With CT imaging the absolute size of the tumor can be measured. This information can be used by the physician to calculate the number of lesions that need to be made. In some embodiments, an exact measurement of the tumor is not needed, since the tumor is viewed with respect to the image of the positioning tool. The physician can then outline the tumor with one or more positioning tools. The resultant lesion that forms needs to have a perimeter that is beyond the tumor dimensions.

Figure 8A:
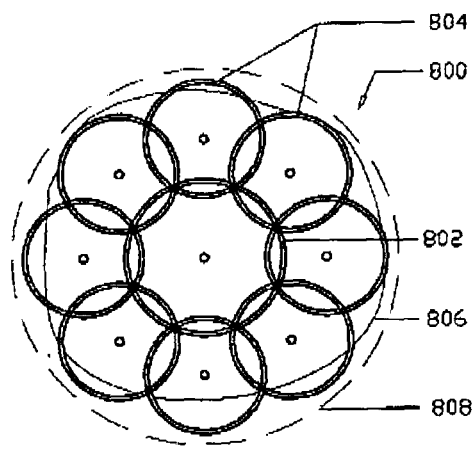
FIG. 8A is a top view of a plurality of positioning tools, in accordance with one embodiment of the present invention, for positioning treatment devices for the treatment of a tumor.

As an example of the embodiment of the present invention a method is disclosed for treatment of a tumor using a kit containing various positioning tools. The kit comprises positioning tools of different sizes and shapes with each tool defining the lesion size the physician can make. The kit has a modular design and positioning tools with different shapes can fit together like a jigsaw puzzle to match a specific tumor. The method of the present invention comprises viewing the tumor under fluoroscopy and placing positioning tools 804 and 802 on the patient's skin such that they overlay the fluoroscopic image of the tumor 806 as illustrated in FIG. 8A. In an example of the present embodiment a larger positioning tool 802 can be placed to cover a substantial portion of the tumor and smaller positioning tools 806 can be placed around its periphery to cover the entire tumor. The shapes can be arranged in order to allow the resultant lesions to overlap to form a lesion with margins 808 that extends beyond the tumor boundary. This differs from the current techniques which place a probe in the centre of the tumor area and use ablation at maximum power. The embodiment of the present invention allows for placement of probes to efficiently target the tumor.

In one example of the embodiment of the present invention, introducers can be used which have depth markings on them. The physician can obtain a side view of the tumor and position the probe appropriately.

In a broad embodiment of the present invention a method is disclosed adding an absolute frame of reference to an image with a relative scale. A problem that is encountered in medical procedures is that the body size is variable in humans and the size varies considerably between individuals. The body is of an absolute size however, current imaging techniques create an image of it on a relative scale. This makes it difficult for physicians to customize treatment based on patient size. The medical treatment devices such as probes or cannulas that are used for example to create lesions, create lesions of absolute size. In order to effectively treat a patient, the physician needs to factor in the difference between patient sizes. The positioning tool can be positioned to measure an individual's specific subcutaneous body structure. If for example the body structure such as the sacrum of a patient is 1.5 times that of an average individual, then the physician is required to make 1.5 times as many lesions at the desired location. The embodiment of the present invention allows the user to quickly customize the treatment to each individual in order to increase the effectiveness of the procedure. Generally, the embodiment of the present invention allows a physician to add an absolute frame of reference to a medical image that is relative.

In a fluoroscopic image it is difficult for a user to determine the quantity of lesions to make and the location at which they must be placed. In the embodiment of the present invention, when the positioning tool is placed on the patient, it is at the same magnification as the bone. This allows the physician to select the device that matches the geometry. When the fluoroscopy screen is viewed without the positioning tool, it is difficult to determine whether 3, 4, or 5 lesions are needed.

As an example of this embodiment of the present invention a method is provided for an application for utilizing a positioning tool in the thoracic region of a patient's spine. The lesion requirements are different based on the individual's anatomy. An L-shaped region on the fluoroscope indicates the region that needs to be lesioned. The lesion needs to be created in the region where the transverse process meets the superior articulate process. A kit is provided with a range of sizes of the reniform positioning tool as shown in FIG. 2. Each of these is placed on the patient's skin in order to match the right device to the patient's anatomy. The physician places each of the devices on the patient's skin and observes if the device aligns with the fluoroscopic image of the patient's anatomy and fills the gap on the image. In one example a smaller reniform positioning tool allows to mark one lesion location, whereas, a larger device allows to define at least three treatment locations at edges 206 as shown in FIG. 2A.

Figure 2C:
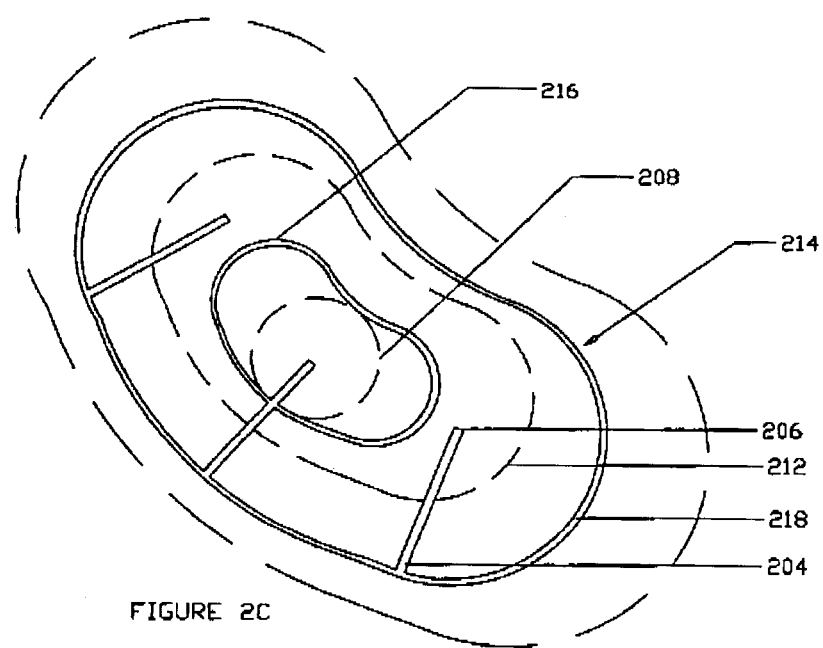
FIG. 2C is a top view of a reniform positioning tool, in accordance with one embodiment of the present invention, depicting different sized positioning tools on a single template.

In an embodiment of the present invention, a positioning tool is provided that comprises a plurality of devices of various sizes. As an example of this embodiment a reniform positioning tool 200 with different sizes is provided on a single template 214. This enables the device to function optimally for a range of sizes of the subcutaneous body structure. This allows the physician to use a single template to match an appropriately sized device size to a patient's subcutaneous body structure. As indicated in FIG. 2C, the inner device 216 can be used to position the treatment device for a patient with relatively small lumbar vertebrae to form a small lesion 208 by placing the probe defined by the edge of the central spacing member. The outer device 218, can be used to form a larger lesion 212, by placing the probe at all available positions defined by all the spacing members.

Figure 9A:
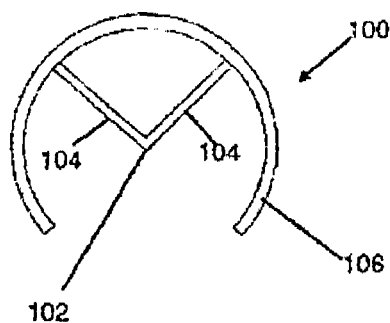
FIGS. 9A-J are top views of still further embodiments of an Epsilon shaped positioning tool, in accordance with one embodiment of the present invention.
Figure 9B:
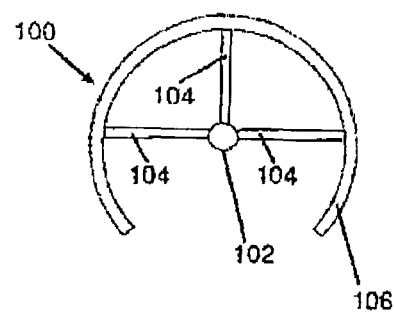
Figure 9C:
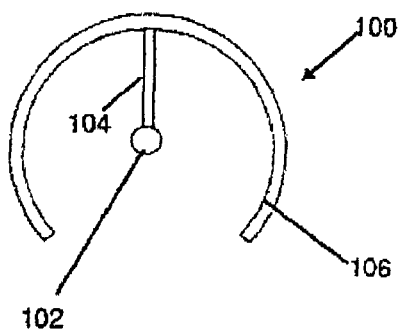
Figure 9D:
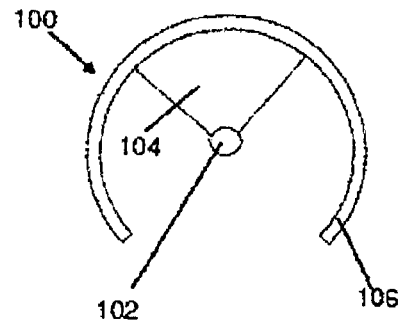
Figure 9E:
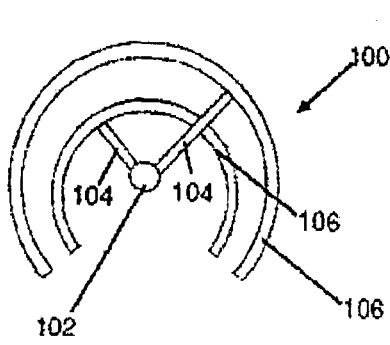
Figure 9F:
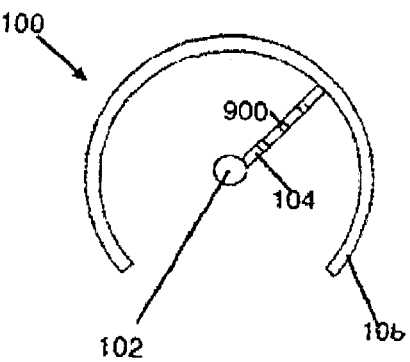
Figure 9G:
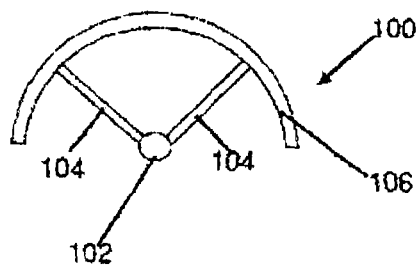
Figure 9H:
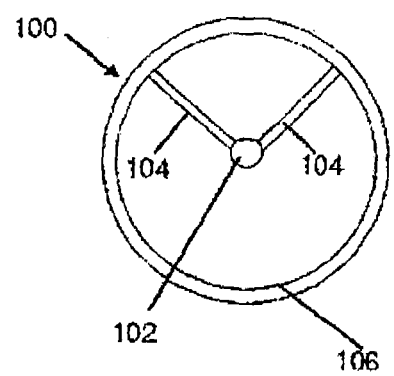
Figure 9I:
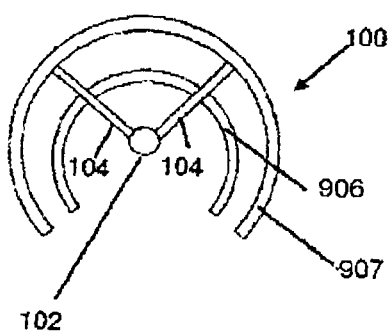

As another example of this embodiment, the device 100 may comprise a plurality of spacing members, each having a different length, as shown in FIG. 9E. Spacing member 104 may be made from any material suitable for use outside a patient's body during a medical procedure, which may or not be radiopaque. For example, spacing member may be made from stainless steel, platinum, titanium, or certain plastics. In some embodiments, device 100 comprises a single circumferential member 106, as shown in FIGS. 9A-9D. In other embodiments, device 100 may comprise more than one circumferential member, for example two circumferential members 906 and 907, as shown in FIG. 9I. In this embodiment, the first circumferential member 906 has a radius equal to the length of spacing member 104, and the second circumferential member 907 has a radius equal to half of the length of spacing member 104. This allows the physician to select the lesion sites best suited to the patient's anatomy.

Figure 8B:
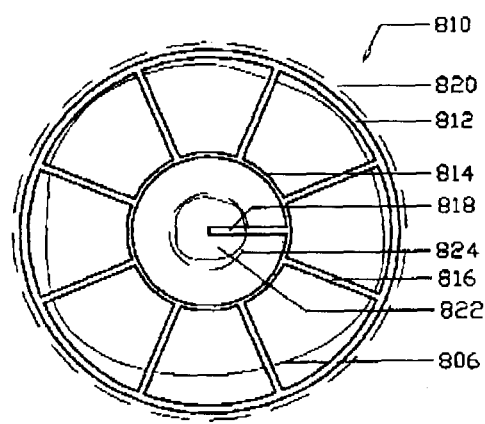
FIG. 8B is a top view of a positioning tool, in accordance with one embodiment of the present invention for positioning treatment devices from the treatment of a tumor, depicting different sized positioning tools on a single template.

As another example of this embodiment of the present invention a circular positioning tool with different sizes is provided on a single template 810. This enables the device to function optimally for a range of sizes of the tumor. This allows the physician to use a single template to match an appropriately sized device size to a specific tumor. As indicated in FIG. 8B, the inner device 814 can be used to position the treatment device for a patient with relatively small tumor 822 to form a small lesion 824 by placing the probe defined by the edge of the central spacing member 818. The outer device 812, can be used to treat a larger tumor 806 by forming a larger lesion 820, by placing the probe at multiple positions defined by spacing members 816.

In another embodiment of the present invention the selection of the marking device with respect to the subcutaneous body structure facilitates the medical treatment procedure by providing information specific to the procedure. The edges of the spacing members on each marking device define the lesion locations. In one embodiment of the present invention each size of the marking device is color coded in order to provide patient-specific procedure information. As an example of the embodiment of the present invention, the information regarding the generator settings or the probe size required is provided. If a larger positioning tool is used, as an example, it may indicate that a particular generator setting with an 18 gauge cannula may be used and more lesions may be made. If the area is smaller, information may be provided to create fewer lesions or to use a smaller gauge cannula such as a 22 gauge. The information can be about generator settings or about the equipment allowing the lesion size to be matched to the geometry. As an example of the embodiment of the present invention, when the appropriate positioning tool has been selected, a bar code on the tool can be scanned, and the correct generator setting can be automatically set.

Figure 1C:
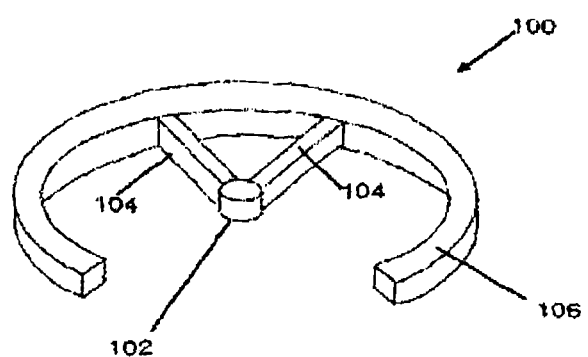
FIG. 1C is a top perspective view of an penannular shaped positioning tool of an embodiment of the present invention.
Figure 1D:
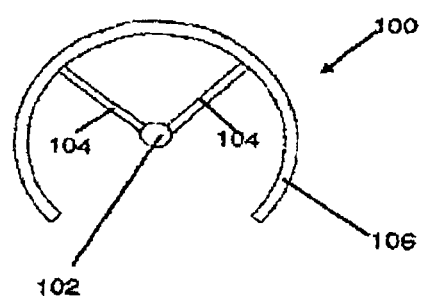

Various embodiments of the positioning tool 100 for use in the Sacroliliac region of a patient's body ore provided. Referring to FIGS. 1C and 1D, an embodiment of a device 100 of the present invention is shown. In the embodiment shown, device 100 comprises an aligning portion 102, two members 104, and a circumferential member 106, collectively referred to as spacing members. Aligning portion 102 may be any member suitable for aligning with a subcutaneous body structure, i.e. for indicating a point on the surface of a body that is aligned with a subcutaneous body structure. In the embodiment shown in FIGS. 1C-1D, aligning portion 102 is circular. In alternate embodiments, aligning portion 102 may be another shape, for example ovoid or square, and the invention is not limited in this regard. In the embodiment shown in FIG. 9A, aligning portion 102 comprises the apex formed by the intersection of first and second members. In further embodiments, aligning portion 102 may comprise an aperture therethrough, for example for passing a needle or other medical instrument therethrough.

Aligning portion 102 is made from a radiopaque material. Suitable materials include, but are not limited to, stainless steels, platinum, or a plastic doped with a radiopaque filler, for example barium, us end.

The device 100 comprises at least one member 104. In the embodiment shown in FIG. 1C-1D, device 100 comprises two members. In alternate embodiments, other numbers of members may be suitable. For example, the embodiment of FIG. 9B comprises three members 104, and the embodiment of FIG. 9C comprises one member 104. Each member 104 comprises an element for indicating a radial distance from aligning portion 102, and thus from a subcutaneous body structure. In some embodiments, spacing element 104 may be elongate, for example rectangular, as shown in FIGS. 9A-9C. In alternate embodiments, member may be another shape. For example, as shown in FIG. 9D, member 104 is a sector of a circle. The length of member 104 may vary depending on the particular application, and the invention is not limited in this regard. As used herein, the 'length' of member 104 refers to the distance member 104 extends away from aligning portion 102 (e.g. in the embodiment of FIG. 9D, the 'length' is the radius of the sector). In some embodiments, for example during certain sacroiliac procedures, member 104 may be between about 0.5 cm and about 2 cm in length. In one particular embodiment, member may be about 1 cm in length.

In some embodiments, member(s) 104 comprise one or more indicators 900 for indicating a particular fraction of the length of member(s) 104. For example, as shown in FIG. 9F, member 104 comprises notches 900 for indicating each quarter of the length of member 104. In alternate embodiments, rather than notches, indicator(s) 900 may comprise dots, lines, or bumps, for example.

Device 100 comprises at least one circumferential member 106, for indicating a circumference associated with the radial distance defined by the length of member 104. That is, circumferential member(s) 106 comprise(s) at least an arc of a circle, having a radius equal to the length of member 104. As shown in FIGS. 9A-9F, circumferential member 106 may comprise an arc consisting of approximately 75% of a circle. In alternate embodiments, circumferential member 106 may comprise an arc consisting of other portions of a circle, for example 50% of a circle, as shown in FIG. 9G. Alternatively, as shown in FIG. 9H, circumferential member 106 may consist of the entirety of the circumference of a circle. The width of circumferential member 106, i.e. the difference between its outer diameter and inner diameter, may vary depending on the application, and the invention is not limited in this regard. In some embodiments, the width may be between about 0.2 mm and about 3 mm. In one particular embodiment, the width may be 2 mm. In alternate embodiments, the width may vary along the circumference of circumferential member 106.

Figure 9J:
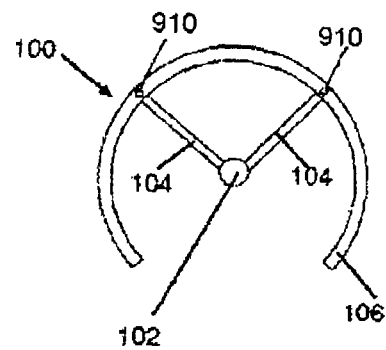

In some embodiments, circumferential member 106 may comprise one or more apertures 910, as shown in FIG. 9J. Such apertures may be used, for example, for a needle or probe to pass therethrough. Alternatively, circumferential member 106 may comprise notches, or another suitable indicator, for showing a particular circumferential position. Circumferential members 106, 906 and 907 may be made from any material suitable for use outside a patient's body during a medical procedure, which may or may not be radiopaque. For example, circumferential member 106 may be made from stainless steel, platinum, titanium, or certain plastics.

The height of device 100 may depend on the particular application. As used herein, 'height' refers to the dimension perpendicular to the plane in which circumferential member 106 is defined. In some embodiments, the height of each of aligning member 102, spacing member 104, and circumferential member 106 may be aligning member 102, spacing member 104, and circumferential member 106. In some embodiments, the height of aligning member 102, spacing member 104, and circumferential member 106 may be between about 0.5 mm and about 3.0 mm. In one particular embodiment, each of aligning member 102, spacing member 104, and circumferential member 106 may be about 1 mm in height In some embodiments, all or a portion of device 100 may be coated with an electrically insulative material, in order to prevent electrical shock. That is, if device 100 is electrically conductive, and is being used during an electromedical procedure, it may be desired to coat device 100 with an electrically insulative material, in order to prevent electricity from being conducted from an electromedical instrument to device 100. For example, device 100 may be coated with polyteirafluoroethylene (Teflon®), or polyetheretherketone (PEEK)

In some embodiments, an adhesive may be applied to a portion of device 100, such that it may adhere to a patient's skin and resist movement. For example, a biocompatible or medical grade adhesive such as a silicone adhesive or an acrylic co-polymer may be applied to a bottom portion of device 100.

In some embodiments, aligning portion 102, member(s) 104, and circumferential member(s) 106 may be made from a single piece of material. For example a single piece of metal may be cut or stamped to form device 100. Alternatively, the components of device 100 may be made separately, for example by stamping, and may be adhered together, for example by gluing or welding.

A method of use of device 100 will presently be described. It is to be noted that the particular method described is meant to be an example only, and device 100 is not limited to any particular method of use.

Device 100 may be used to indicate a position on the surface of the body relative to a subcutaneous body structure, for example a foramen of a bone. In one embodiment, device 100 may be used during a radiofrequency neurotomy procedure in the sacroiliac region of the patient's body, for example as described in U.S. patent application Ser. No. 11/428,458, incorporated herein by reference. In such a procedure, it may be required to insert an electromedical probe into the patient's body at a particular distance from the lateral edge of a target foramen. In some embodiments, this distance may be about 1 cm, thus a user may select a device 100 having spacing member(s) 104 of length 1 cm. In a first step of the method, with the patient lying prone, a user may place device 100 on the rear surface of the patient's body, in the region of the target foramen. Using fluoroscopy, the user may visualize the sacrum of the patient's body from the posterior view. This view will show the sacrum, including the target foramen. Due to the radiopacity of aligning member 102, aligning member 102 will appear on the fluoroscopic image. The user may then move device 100 around on the patient's body until aligning member is aligned with, i.e. above, the lateral edge of the target foramen, as shown in the fluoroscopic image.

In some embodiments, it may be difficult to view the target foramen under fluoroscopy, and thus it may be difficult to align device 100 with the lateral edge of the foramen. In these embodiments, a user may insert a guiding needle posteriorly into the sacrum, in the region of the target foramen. The user may 'feel around' with the needle until the tip of the needle is located at the lateral edge of the foramen. The user may then visualize the sacrum from the posterior view using fluoroscopy. In the fluoroscopic image, the guiding needle will 'point to' the lateral edge of the foramen. The user may then place device 100 on the surface of the patient's body, and move device 100 around on the patient's body until aligning member is aligned with, i.e. above, the tip of the guiding needle, as shown in the fluoroscopic image.

When device 100 is in place, circumferential member 106 will indicate the boundary of the region that is 1 cm away from the aligning member 102, and thus the region that is 1 cm away from the lateral edge of the foramen. The user may then insert the probe into the patient's body at a position adjacent circumferential member 106, e.g. the edges of member 106, referred to as instrument positioning portions. Such a position may be on the outside of circumferential member 106, or on the inside of circumferential member 106. Alternatively, the user may insert the probe through an aperture 910 in circumferential member 106. These embodiments will allow for the probe to be inserted approximately 1 cm away from the lateral edge of the foramen.

In a further embodiment, the user may wish to insert more than one probe, and may wish for each probe to be at a particular circumferential position, in addition to a particular radial position. For example, the user may wish to insert three probes, each probe being about 1 cm away from the lateral edge of the foramen, and being about 90 degrees away from each-other. In this embodiment, the user may select a device in which the spacing members 104 are structured such that they 'point' to a particular circumferential position. For example, in the embodiment shown in FIG. 9B, spacing members 104 are at 90 degrees relative to each-other. Thus the user may insert the probes adjacent circumferential member 106, such that each probe is aligned with a spacing member. This would allow for each probe to be positioned about 1 cm away from the lateral edge of the foramen, and 90 degrees away from each-other.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A non-invasive positioning tool configured for external placement on a surface of a patient's skin so as to aid in the positioning of at least one instrument at a subcutaneous treatment site visible via images acquired using a medical fluoroscopy imaging device, the positioning tool comprising:
    a penannular-shaped member having two edges, each edge defining an instrument positioning portion, at least one spacing member having a proximal end attached at the center of the penannular-shaped member and a distal end spaced from the proximal end and defining a length therebetween, wherein the combination of the penannular-shaped member and the at least one spacing member form an epsilon-shape positioning tool, at least one aligning portion attached at the distal end of the at least one spacing member and configured for aligning the positioning tool with a target on the treatment site visible via the images acquired using the medical fluoroscopy imaging device such that the positioning tool is configured for external placement on a surface of the patient's skin, wherein the at least one spacing member is radiopaque, wherein the radiopacity of the at least one spacing member varies along the length of the spacing member by having different metals with distinct radiopacities between them, wherein the cross-section of the spacing member is shaped to have a triangular void in the center of the spacing member along its length, and wherein the at least one spacing member comprises a plurality of notches having a predetermined spacing so as to provide visible incremental measurement information under the fluoroscopic imaging;
    wherein the at least one aligning portion being further visible via the images acquired using the medical fluoroscopy imaging device and spaced from the instrument positioning portions and;
    the instrument positioning portions being visible via the images acquired using the medical fluoroscopy imaging device for providing radiopaque indicator for positioning the at least one instrument at the target on the subcutaneous treatment site.

2. The positioning tool of claim 1, wherein the at least one aligning portion and the instrument positioning portions are radiopaque.

3. The positioning tool of claim 1, further comprising a securing means for configured to securing the positioning tool to a surface of a patient's body.

4. The positioning tool of claim 3, wherein the securing means comprises at least one projection extending from at least one of the at least one spacing member and the at least one aligning portion.

5. The positioning tool of claim 4, further comprising a plurality of projections extending perpendicularly from at least one of the at least one aligning portion and the at least one spacing member.

6. The positioning tool of claim 3, wherein the securing means comprises an adhesive material located on a surface of at least one of the at least one aligning portion and the at least one spacing member.

7. The positioning tool of claim 3, wherein the securing means comprises a layer of material at least partially composed of silicone.

8. The positioning tool of claim 1, further comprising a wedge-shaped member removably coupled to at least one of the at least one aligning portion and the at least one spacing member for adjusting an angle of the at least one of the at least one aligning portion and the at least one spacing member configured to be relative to a surface of a patient's body.

9. The positioning tool of claim 1, wherein the at least one aligning portion comprises a reniform shape.

10. The positioning tool of claim 1, wherein the at least one aligning portion comprises an edge defined by the at least one spacing member.

11. The positioning tool of claim 1, further comprising a plurality of the penannular-shaped members.

12. The positioning tool of claim 11, wherein each penannular-shaped member defines a radius and wherein the radius of one penannular-shaped member differs from the radius of another penannular-shaped member.

13. The positioning tool of claim 1, further comprising a plurality of aligning portions.

14. The positioning tool of claim 1, further comprising a treatment identifier, wherein the treatment identifier comprises a bar code for providing information regarding a treatment procedure to be performed.

15. The positioning tool of claim 1, further comprising a device identifier, wherein the device identifier comprises a colored portion of at least one of the at least one aligning portion and the at least one spacing member for providing to a user information regarding the at least one medical instrument to be used.

16. A kit comprising:
    a plurality of non-invasive positioning tools configured for external placement on a surface of a patient's skin so as to aid in tile positioning of at least one instrument used to treat a subcutaneous treatment site visible via the images acquired using a medical fluoroscopy imaging device, each positioning tool comprising a penannular-shaped member having two edges, each edge defining an instrument positioning portion, at least one spacing member having a proximal end attached at the center of the penannular-shaped member and a distal end spaced from the proximal end and defining a length therebetween, wherein the combination of the penannular-shaped member and the at least one spacing member form an epsilon-shape positioning tool, at least one aligning portion attached at the distal end of the at least one spacing member and configured for aligning the positioning tool with a target on the treatment site visible via the images acquired using the medical fluoroscopy imaging device such that the positioning tool is configured for external placement on a surface of the patient's skin, wherein the at least one spacing member is radiopaque, wherein the radiopacity of the at least one spacing member varies along the length of the spacing member by having different metals with distinct radiopacities between them, wherein the cross-section of the spacing member is shaped to have a triangular void in the center of the spacing member along its length, and wherein the at least one spacing member comprises a plurality of notches having a predetermined spacing so as to provide visible incremental measurement information under the fluoroscopic imaging;

wherein the at least one aligning portion being further visible via the images acquired using the medical fluoroscopy imaging device and spaced from the instrument positioning portions and;

the instrument positioning portions being visible via the images acquired using the medical fluoroscopy imaging device for providing a radiopaque indicator for positioning the at least one instrument at the target on the subcutaneous treatment site, wherein each of the plurality of positioning tools is of a different size.

17. A method of positioning at least one medical instrument at a subcutaneous treatment site visible via images acquired using a medical fluoroscopy imaging device and further with the aid of non-invasive positioning tool, the method comprising:

positioning a non-invasive positioning tool on an exterior surface of a patient's skin, the positioning tool comprising a penannular-shaped member having two edges, each edge defining an instrument positioning portion, at least one spacing member having a proximal end attached at the center of the penannular-shaped member and a distal end spaced from the proximal end and defining a length therebetween, wherein the combination of the penannular-shaped member and the at least one spacing member form an epsilon-shape positioning tool, at least one aligning portion attached at the distal end of the at least one spacing member and configured for aligning the positioning tool with a target on the treatment site visible via the images acquired using the medical fluoroscopy imaging device such that the positioning tool is configured for external placement on a surface of the patient's skin, wherein the at least one spacing member is radiopaque, wherein the radiopacity of the at least one spacing member varies along the length of the spacing member by having different metals with distinct radiopacities between them, wherein the cross-section of the spacing member is shaped to have a triangular void in the center of the spacing member along its length, and wherein the at least one spacing member comprises a plurality of notches having a predetermined spacing so as to provide visible incremental measurement information under the fluoroscopic imaging;

aligning the positioning tool with the target visible via the images acquired using the medical fluoroscopy imaging device by visualizing the aligning portion and the spacing portion in the images;

inserting the at least one medical instrument into the patient's body; and positioning the at least one medical instrument into the patient's body such that a treatment portion of the at least one medical instrument is aligned with the instrument positioning portions, by visualizing the treatment portion and the instrument positioning portions using the images acquired using medical fluoroscopy imaging device.

18. The method of claim 17, wherein the treatment site comprises a tumor.

19. The method of claim 17, wherein the treatment site comprises a region of a sacrum of the patient's body.

20. The method of claim 19, wherein the target comprises a needle inserted at a posterior sacral foramina of the sacrum.

21. The method of claim 17, wherein the treatment site comprises spinal tissue.

22. The method of claim 21, wherein the spinal tissue comprises neural tissue located at a portion of the spine selected from the group consisting of a cervical portion, a lumbar portion and a thoracic portion.

23. The method of claim 17, wherein the step of aligning comprises aligning the aligning portion with the target in at least two planes.

* * * * *